May 16, 1972 W. W. KNICELY ET AL Plant Pat. 3,171
AZALEA PLANT
Filed July 20, 1970
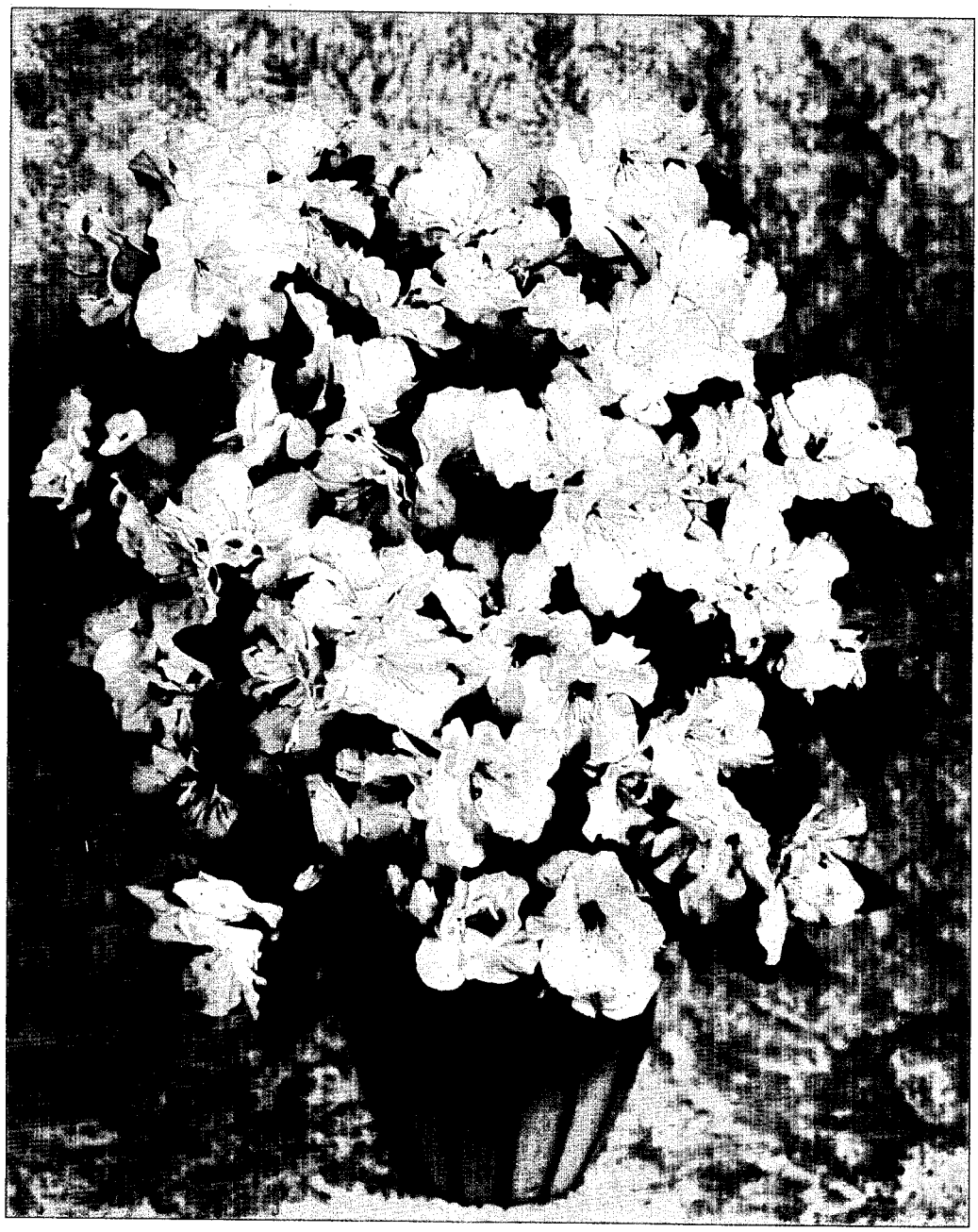
INVENTORS: WALTER W. KNICELY
& WILLIAM E. DUFFETT
BY Oberlin, Maky, Donnelly & Renner
ATTORNEYS

United States Patent Office

Plant Pat. 3,171
Patented May 16, 1972

3,171

AZALEA PLANT

Walter W. Knicely, Barberton, and William E. Duffett, Akron, Ohio, assignors to Yoder Brothers, Inc., Barberton, Ohio

Filed July 20, 1970, Ser. No. 56,759
Int. Cl. A01h *5/00*
U.S. Cl. Plt.—56 1 Claim

The present invention comprises a new and distinct variety of azalea plant which has resulted from crossing certain azalea selections in a program of hybridization. The seed parent is unnamed and unpatented, and identified for breeding purposes as seedling #1035. The pollen parent is likewise unnamed and unpatented, and identified for breeding purposes as seedling #1040.

The new variety is similar in certain respects to Skylark, an unpatented but well-known commercial variety, having the same characteristics as Skylark of rapid growth, keeping quality and evergreen foliage. The new variety is distinguished from Skylark by the following characteristics:

(1) The new variety buds easier and more uniformly than Skylark.

(2) The new variety though vigorous growing has no tendencies toward irregular shoot differentiation and wild growth, as compared to Skylark, and needs no growth regulator. Skylark usually needs a growth regulator to control wild growth.

(3) The new variety responds (buds) earlier by several weeks when compared with Skylark in both natural and year round programs.

(4) The new variety has at least a week longer keeping quality in the home than Skylark.

(5) The new variety is a lighter pink color than Skylark.

The new variety was selected from progeny of seedlings from the above mentioned parents. Varietal worth was determined by flowering liners built up from the initial selection in both year round and natural season developmental flowering programs over a period of four years. Stock growth was evaluated in the vicinity of Fort Myers, Fla.

My new variety has been asexually reproduced by cuttings at Barberton, Ohio, and has been found to retain its distinctive characteristics through successive propagations.

My new variety when grown in the vicinity of Barberton, Ohio has a response described as early-mid season in natural programs and early season in year round programs. It will, however, be understood that the response time and blooming period may vary significantly with varying environmental conditions such as temperature and amount of daylight. Suggested flowering period is from mid-December through April in a natural season program and year-round (all 12 months) in a controlled flowering program.

The accompanying drawing shows the unique features of my new variety, the colors being as nearly true as possible with color illustrations of this type.

The following is a detailed description, including color designations of my new variety, based on observations made of the new variety in a greenhouse in Barberton, Ohio. The color references are to the Munsell Color Book, 1963 edition:

*Botanical classification: Rhododendron hybrida,* evergreen type.

*Flower:*

*Color.* — Rose pink — general tonality — rose pink 6.25RP5/14—sepals first divide—rose pink 8.75 RP4/12—petals unfurl—rose pink 6.25RP5/14—fully open—rose pink, lighter than 6.25RP5/14—inside petals—rose pink 6.25RP5/14—reverse petals—rose pink, lighter than 6.25RP5/14—base of petals — salmon pink, near 2.5R7/8 — blotch—slightly darker than general base color 6.25RP5/14; outer hose not completely petaloid, rose pink 6.25RP5/14 with the pink near 7.5RP8/4 and green blotches 5GY5/6 — discoloration — retains color for 3 weeks followed by gradual fading. Bright greenhouse will speed fading.

*Bud.* — Size — medium — form — conoidal—opening habit—fully expanded petals rose bud-like; open, cup-like, retains cupped form.

*Bloom.* — Size — medium-large; average — 2⅝"; range—2¼"–3"—borne—several together; average 3, range 1–4—form—semi-double with varying number of petaloid anthers; calyx of individual flowers petaloid to varying degrees.

*Blooming habit.*—Once, profusely.

*Response.*—Natural season early. Christmas flowering possible all areas. Year round-early. Sets buds easily and uniformly under a wide range of conditions.

*Sepals.*—Normal, smooth, somewhat hairy, persistent.

*Peduncle.*—Length—long; aspect, hairy; strength, strong.

*Petals.*—Texture—soft—appearance—inside, satiny; outside, satiny—form—rounded wavy margins—arrangement — imbricate with petaloids — fragrance — none — persistence—hang on and dry; non-shatter — longevity — greenhoue, 3 weeks; home 4 weeks.

*Reproductive organs.*—Stamen anthers—5–10 many petaloid, tannish pink, near 7.5YR7/4 — filaments—thin, pubescent, light pink 10RP7/4—style—generally columnar; may be fasciated, pink 10RP6/10—stigmas—generally normal, may be fasciated, tan near 5YR6/6—ovaries—hypogynous.

Plant: Bush form.

*Growth habit.*—Spreading, compact, horizontal, with growth regulators not beeing needed for compact growth and budding.

*Breaking habit.*—Vigorous with no wild growth tendencies.

*Size.*—Of average finished product grown from the standard #7 liner of Yoder Brothers, Inc., Barberton, Ohio.

*Budding ease.*—Excellent under wide range of environmental conditions.

*Uniformity of budding.*—Excellent.

*Foliage.*—leaflets—single—size—length, 2–2½", average 2¼"; width, 1–1¼", average 1"—texture—upper, glossy; lower, smooth—rib and veins—slightly depressed—edge—nearly smooth—color—new foliage, upper, light yellow green 7.5GY4/6, lower, light green near 7.5GY6/4; mature foliage upper, dark green 7.5GY3/4, lower, green 7.5GY5/4 — petiole — short, hairy, light green 5GY7/16.

*Stems.*—Color—New wood, green 5GY6/6; mature wood, light brown, darker than 10YR5/4.

*Recommended flowering period*—year round, all year; natural season, mid-December–April.

*Responsiveness to day length and temperature.*—Buds and flowers under wide range of conditions.

*Cooler tolerance.*—Excellent.

*Shipping tolerance.*—Excellent.

I claim:

1. A new and distinct variety of azalea characterized particularly as to novelty by its rapid growth and good size increase, its uniform and easy budding, its earliness in natural season flowering programs, its rose-pink color, its long-lastingness and its adaptibility to year round flowering programs under wide and varied conditions.

No references cited.

ROBERT E. BAGWILL, Primary Examiner